BEST AVAILABLE COPY
PLANT
rch 28, 1950
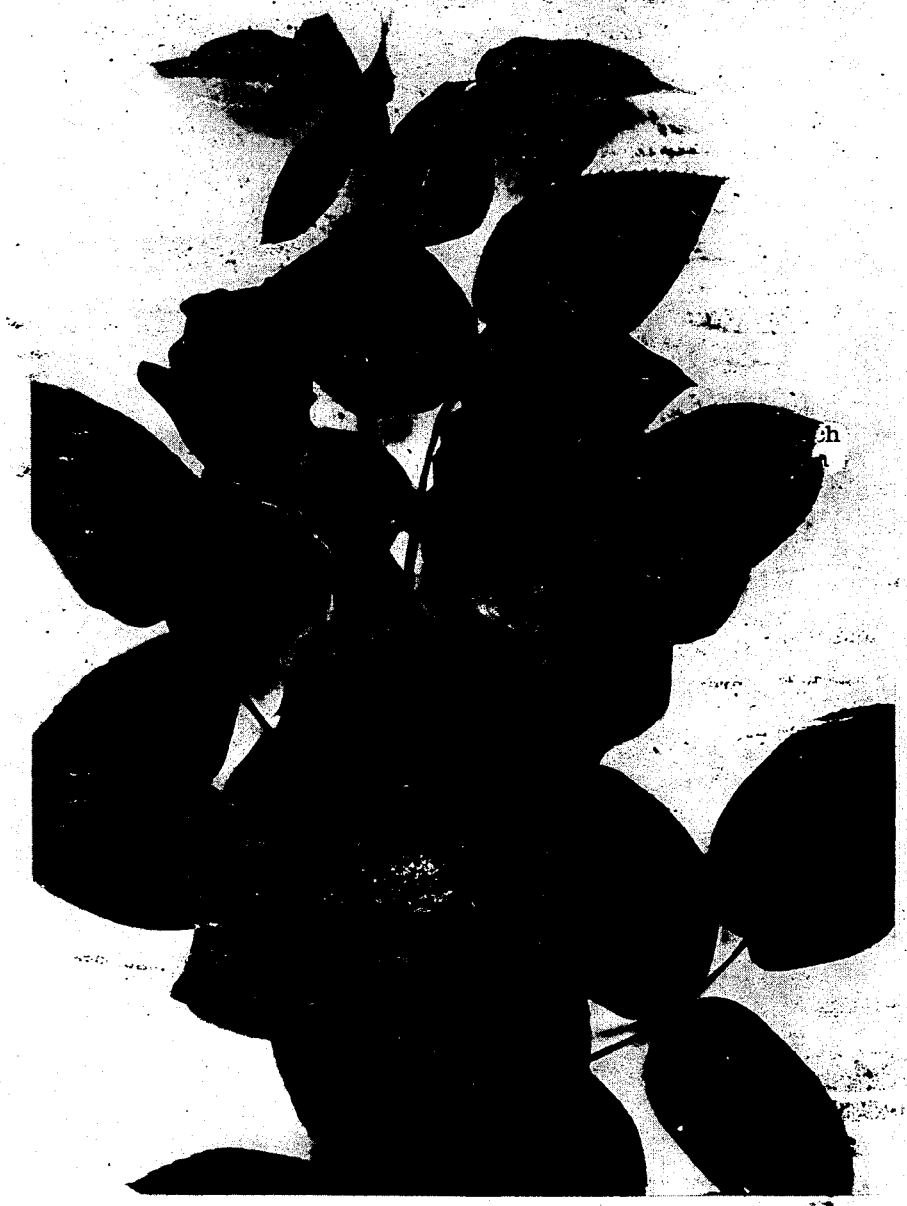
Inventor.
Jean Gaujard
By: Robert Cobb
attorneys.

BEST AVAILABLE COPY

UNITED STATES PATENT OFFICE 1,017

ROSE PLANT

Jean Gaujard, Feyzin, France, assignor to Jackson & Perkins Company, Newark, N. Y., a corporation of New York Application March 28, 1950, Serial No. 152,370

1 Claim. (Cl. 47—61)

The present invention relates to a new and distinct variety of rose plant of the hybrid tea class, originated by crossing a selected seedling of an unnamed seedlings×"Capucine Bicolor" (unpatented) and a selected seedling of an unnamed seedling×"Georges Chesnel" (unpatented).

The primary objective in making this cross is to obtain a better color and flower on the vigorous bushes of the two unnamed seedlings. This objective was attained to a marked extent, evidenced by the enlargement of the yellow color at the base of the petals as derived from the "Capucine Bicolor" variety, and by the vigorous growth and free blooming habit of the new variety, thereby showing a transference of characteristics from both parents.

Besides the unique coloring characteristic which is particularly evident in the bud and the half-open flower of the new variety, a further important characteristic of the new variety is the interesting and unique suffusion of the Lemon Chrome color at the base of the petals into the petals, which distinguishes the new variety from a true bicolor rose, and still further points to a distinct heritage from one of its bicolor parents.

Another important characteristic of this new variety is the translucent effect of the rose red color of the open bloom.

A sexual reproduction of this new rose variety by budding at Newark, New York, and at Pleasanton, California, shows that the foregoing characteristics come true to form and are established and transmitted through succeeding propagations.

In the drawing are shown specimens of the new rose variety, with the flowers in various stages of development from small bud to full-open bloom.

The following is a detailed description of the new variety with color terminology in accord with Ridgway's Color Standards and Nomenclature:

Parentage: Seedling.

*Seed parent.*—Unnamed seedling (seedling × "Capucine Bicolor").

*Pollen parent.*—Unnamed seedling (seedling ×"Georges Chesnel").

Classification: Botanic and commercial—hybrid tea.

*Flower*

(Observations made in the greenhouse at Newark, New York, in the morning in the month of September, 1949.)

Blooming habit: Recurrent—continuous.

Bud:

*Size.*—Large.

*Form.*—Long pointed. Is not affected by wet or hot weather.

*Color.*—When sepals first divide—Pomegranate Purple, Plate 12. When petals begin to unfurl—between Pomegranate Purple, Plate 12, and Spinel Red, Plate 26. When half blown—inside of petals; Spectrum Red, Plate 1, overcast with Rose Red, Plate 12; reverse of petals; Rose Red, Plate 12 suffused with Light Cadmium, Plate 4, from the base of the petal.

*Sepals.*—Branched. Curl back when petals begin to unfurl. Color—inside: Clear Fluorite Green, Plate 32; outside: Parrot green, Plate 6.

*Calyx.*—Shape—apple. Size—large. Aspect—smooth. Odor when rubbed—None. Color—Lettuce Green, Plate 5.

*Peduncle.*—Length—medium. Aspect—smooth. Color—Yellowish Green, Plate 5. Strength—erect; slender.

*Opening.*—Opens up well. Is not affected by adverse weather conditions.

Bloom:

*Size.*—Large. Average size when fully expanded, 4½" to 5".

*Borne.*—Singly.

*Stems.*—Medium length; strong.

*Form.*—When first open—high center. Permanence—retains its high-centered form to nearly the end; then flattens.

*Petalage.*—Double (full but open center). Number of petals under normal conditions, 25.

*Color.*—Center of flower—Rose Red, Plate 12. Outer petals—Rose Red, Plate 12, overcast with Tyrian Rose, Plate 12. Inside of petals—Rose Red, Plate 12, lightly overcast with Tyrian Rose, Plate 12. Reverse of petals—Rose Color, Plate 12, overcast with Deep Rose Pink, Plate 12, with the lower half of the petal suffused with Lemon Chrome, Plate 4, from the base of the petal. General tonality from a distance—Rose Red, Plate 12, overcast with Tyrian Rose, Plate 12.

*Discoloration.*—General tonality at end of first day—Rose Red, Plate 12. Second day—Rose Red, Plate 12, lightly overcast with Tyrian Rose, Plate 12. Third day—Rose Red, Plate 12, overcast with Tyrian Rose, Plate 12.

BEST AVAILABLE COPY

Petals:

*Texture.*—Thin. Is not affected by wet or hot weather.

*Appearance.* — Inside — satiny. Outside — shiny.

*Form.*—Oval.

*Arrangement.*—Informal. (with "rags" in center). Petaloids in center—few; large.

*Persistence.*—Drop off cleanly.

*Fragrance.*—Moderate. Nature—tea (average hybrid tea scent).

*Lasting quality.*—On the plant and as cut flower—long.

Genital organs:

*Stamens, anthers.*—Large; many. Color—Empire Yellow, Plate 4. Arrangement—regular around styles.

*Stamens, filaments (threads).* — Long. Color—Lemon Chrome, Plate 4.

*Pollen.*—Color—Buff Yellow, Plate 4.

*Styles.*—Loosely separated, uneven length; short; thin.

*Stigmas.*—Color—Apricot Yellow, Plate 4.

*Ovaries.*—All enclosed in calyx.

*Plant*

Form: Bush.

Growth: Vigorous; upright.

Foliage: 3 to 5 leaflets.

*Size.*—Large.

*Quantity.*—Abundant.

*Color.*—*New foliage*—Upper side: Oil Green, Plate 5, overlaid with Oxblood Red, Plate 1. Serrations Oxblood Red, Plate 1; under side: Light Cress Green, Plate 31, overlaid with Oxblood Red, Plate 1. *Old foliage*—upper side: Cress Green, Plate 31; under side: Rainette Green, Plate 31.

*Shape* [illegible] ed.

*Texture* [illegible] side — leat[illegible] v. [illegible] r side—sm[illegible] s and veins—ord[illegible] y.

*Edge.*—Serrated (saw toothed).

*Serration.*—Single; small.

*Leaf stem.*—Color—Absinthe Green, Plate 31. Under side—smooth.

*Stipules.*—Long; smooth.

*Disease resistance.*—Resistant.

Wood:

*New wood.*—Color—Yellowish Oil Green, Plate 5. Bark—smooth.

*Old wood.*—Color—Jade Green, Plate 31. Bark—smooth.

Thorns:

*Thorns.*—Quantity—on main stalks from base and on laterals from stalk—ordinary. Form—broad base; medium length; hooked downward. Color when young—Oxblood Red, Plate 1. Position—irregular.

*Prickles* and *short needles.*—None.

I claim:

A new and distinct variety of rose plant of the hybrid tea class, characterized as to novelty by its vigorous growth and free blooming habit, by the enlarged lemon chrome color at the base of the petals and the suffusion of such color into the petals, particularly evidenced in the bud and half-open flower, and by the translucent effect of the rose red color of the open blooms, substantially as shown and described.

JEAN GAUJARD.

No references cited.